United States Patent [19]

Fincke et al.

[11] Patent Number: 5,249,573
[45] Date of Patent: Oct. 5, 1993

[54] DEFIBRILLATION DISCHARGE CIRCUIT TEST

[75] Inventors: Randall W. Fincke, Winchester; Michael L. Lopin, Newton, both of Mass.

[73] Assignee: ZMD Corporation, Wilmington, Del.

[21] Appl. No.: 839,954

[22] Filed: Feb. 21, 1992

[51] Int. Cl.$^5$ .............................................. A61N 1/00
[52] U.S. Cl. ...................................................... 607/6
[58] Field of Search .................................. 128/419 D

[56] References Cited

U.S. PATENT DOCUMENTS 4,628,935  12/1986  Jones et al. ............... 128/419 D
5,033,467  6/1991   Bocchi et al. ............. 128/419 D

OTHER PUBLICATIONS

Sum and Dewhurst, "Digtal cardiac defibrillator tester," Nov. 1979, 710–714, *Medical and Biological Engineer and Computers*, vol. 17, No. 6.

*Primary Examiner*—Lee S. Cohen
*Assistant Examiner*—Marianne Parker
*Attorney, Agent, or Firm*—Fish & Richardson

[57] ABSTRACT

Method and apparatus for discharging a defibrillation discharge circuit 30 across a short circuit load 166 for monitoring defibrillation pulses 180 generated by the circuit to test that the pulses are acceptable. The discharge circuit 30 comprises an electrical capacitor 34 for storing defibrillation pulse energy and an electrical inductor 38 in series with the capacitor for shaping the discharge pulses. In the invention, parameters representative of the shape of the defibrillation pulse are detected as the pulse is discharged and are compared to predetermined values characteristic of the shape of an acceptable pulse. Based on the outcome of this comparison, an output is provided indicating whether the pulse is acceptable.

24 Claims, 8 Drawing Sheets

DEFIBRILLATION DISCHARGE CIRCUIT TEST

BACKGROUND OF THE INVENTION

This invention relates to transcutaneous pacemakers and defibrillators.

Emergency techniques for cardiac therapy are essential for successfully treating life threatening cardiac conditions. The most common of such conditions is ventricular fibrillation, in which the electrical pulse generators in the cardiac muscle fibrillate asynchronously, causing chaotic muscle contraction. The other common cardiac threat is loss of pacing, in which the pacing stimulus nerves of the cardiac muscle fail to initiate contraction of the muscle.

Ventricular fibrillation is treated with a high energy electrical pulse, called a defibrillation pulse, which is transcutaneously delivered to the heart to resynchronize the heart's pulse generators. Loss of pacing is treated using a transcutaneous pace maker to deliver pacing current pulses to the heart and thereby maintain cardiac contractions.

Frequently a patient in cardiac distress experiences both the conditions of fibrillation and loss of pacing. In order to most efficiently treat this situation, both defibrillation and external pacing equipment are typically combined in a single portable instrument for emergency personnel convenience. Such an instrument includes a pair of transcutaneous pacing electrodes and corresponding pacing circuitry, as well as a pair of defibrillation electrodes and corresponding defibrillation circuitry. In addition, the instrument may include a specialized multifunction electrode pair which can deliver both pacing and defibrillation pulses when used with appropriate connections to the pacing and defibrillation circuitry.

Typically, a hardware relay scheme isolates operation of the pacing circuitry from the defibrillation circuitry to thereby isolate the circuitry outputs. When separate pairs of pacing and defibrillation electrodes are used with the circuitry, the relay scheme decouples the two circuits. Conversely, when the multifunction electrode pair is used, the relay scheme couples the circuits to a common output so that the pacing stimuli and defibrillation pulses may be delivered to a single electrode pair. Such relays, being required to withstand the defibrillation pulse, are quite bulky and rather expensive, and must be isolated from any surrounding transformers that could trigger their activation.

Defibrillation electrodes are usually mounted one each on a hand-held paddle which includes a pressure-activated switch for initiating the defibrillation discharge of energy to a patient. Because this energy is high enough to be lethal if delivered at the wrong time or to the wrong location, the paddle switches are both connected in series with the discharge circuitry. If one switch is unintentionally activated alone, no discharge will result; only the simultaneous activation of both switches will initiate a discharge. However, if one switch is held closed (activated) as a result of a hardware malfunction, activation of the other switch would result in unintentional defibrillation discharge. Without the ability to monitor the open and closed state of the switches an operator has no way of verifying the integrity of the switches, and therefore the integrity of the discharge circuit. Moreover, the discharge control circuitry is unable to internally detect a switch malfunction and prevent a corresponding discharge malfunction.

The electrical current generated by the defibrillation discharge circuit for delivery to the patient is typically monitored to check the integrity of the circuit and to study the physiological effects of the discharge. This current may reach as much as 125 A, and the corresponding voltage of the discharge may reach as much as 5000 V. Conventionally, the current is monitored using a current transformer whose primary winding is connected in series with the discharge circuit. The secondary winding of the transformer is then connected to a sensing circuit for measuring the current level. The particular choice of transformer is based on the requirement that the component withstand the high current and voltage levels of the discharge circuit; typically such a transformer is disproportionately larger than the other circuit components and is rather expensive. More importantly, such a transformer generates substantial coupling flux between its primary and secondary windings which can severely impact the operation of neighboring circuits. The transformer must thus be physically isolated from circuits having sensitivity to the coupling flux.

It is desirable to frequently test the defibrillator discharge circuit for functionality, due to the critical nature of the emergency situations in which it is needed. Traditionally, such a test is accommodated by providing a characteristic load resistor, say 50 Ω, into which the circuit may be energized to simulate discharge into a patient. The 50 Ω load resistor is typically contained either within the defibrillator equipment or within a separate testing apparatus, with a connection through the equipment housing for contact to the defibrillator electrodes.

Because the defibrillator discharge's high energy (about 360 j) is delivered in a short time (90% in about 3 msec), the peak power requirement of the load resistor is quite substantial, exceeding 100 KW. The resistor must be, well ventilated because the average power may exceed 30 watts, resulting in significant resistive heating, and typically, some type of customized heat sink is required in the location of the resistor. Additionally, a sizeable resistor is required to withstand the discharge's peak voltage of as much as 2500 V. This physical size may use up a substantial portion of the circuitry housing. The high voltage also requires the electrical connection from the defibrillator electrodes to the resistor to regularly withstand such voltage. Finally, the electrical connection on the equipment housing to the resistor must be isolated to prevent accidental contact by an operator; discharge of the circuit with only one electrode connected to the resistor while an operator touches the resistor would dump the high voltage across the resistor to the operator.

SUMMARY OF THE INVENTION

In general, in one aspect, the invention features a scheme for discharging a defibrillation discharge circuit across a short circuit load for monitoring defibrillation pulses generated by the circuit to test that the pulses are acceptable; the circuit includes a capacitor for storing the discharge pulse energy and an inductor for shaping the pulse. In the invention, parameters representative of the shape of the defibrillation pulse are detected as the pulse is discharged and are compared to predetermined values characteristic of the shape of an acceptable pulse. Based on the outcome of the comparison, an output is provided indicating whether the pulse is acceptable. This scheme eliminates the disadvantages associated with discharging the defibrillation electrodes into a load resistor located internally to the unit housing, as with the shorting bar it is not necessary to penetrate the housing, and provides a more flexible test analysis than the load resistor scheme.

In preferred embodiments, the capacitor is charged to a prespecified pulse energy and then discharged into the short circuit. In further preferred embodiments, a parameter representative of the defibrillation pulse current is detected and sampled to produce sample values; in more preferred embodiments a sense voltage is measured and sampled; the voltage is developed between the ends of a sense winding wound around the inductor with at least one turn; the sense voltage is integrated to determine corresponding pulse current values, and the peak and valley current values are determined. A ratio of the peak to valley current is determined and based on the ratio, any adjustments in the peak current value are made to compensate for temperature-induced changes in inductor winding resistance. In the preferred embodiment, the adjusted peak current value is compared with a range of peak pulse currents and must fall within the range for the pulse to be determined as acceptable.

Other features and advantages of the invention will be apparent from the following description of a preferred embodiment and from the claims.

DESCRIPTION OF THE PREFERRED EMBODIMENTS

Figure 1:
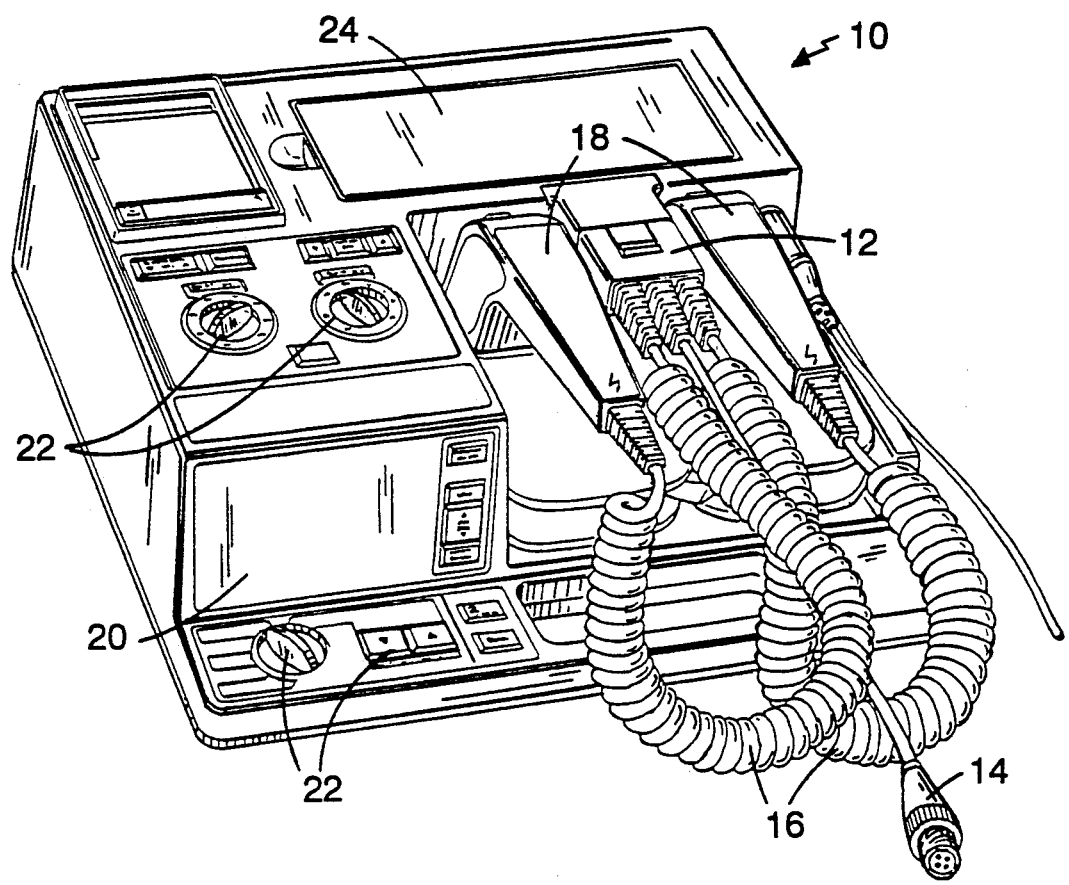
FIG. 1 is a perspective view of a portable transcutaneous pace maker and defibrillator unit.

Referring to FIG. 1, there is shown a portable defibrillator and pacing unit 10 for providing defibrillation energy pulses and transcutaneous pacing stimuli to a patient in cardiac distress. Such a unit is available from Zoll Medical Corporation of Woburn, Mass. under the product name PD1400.

Figure 2:
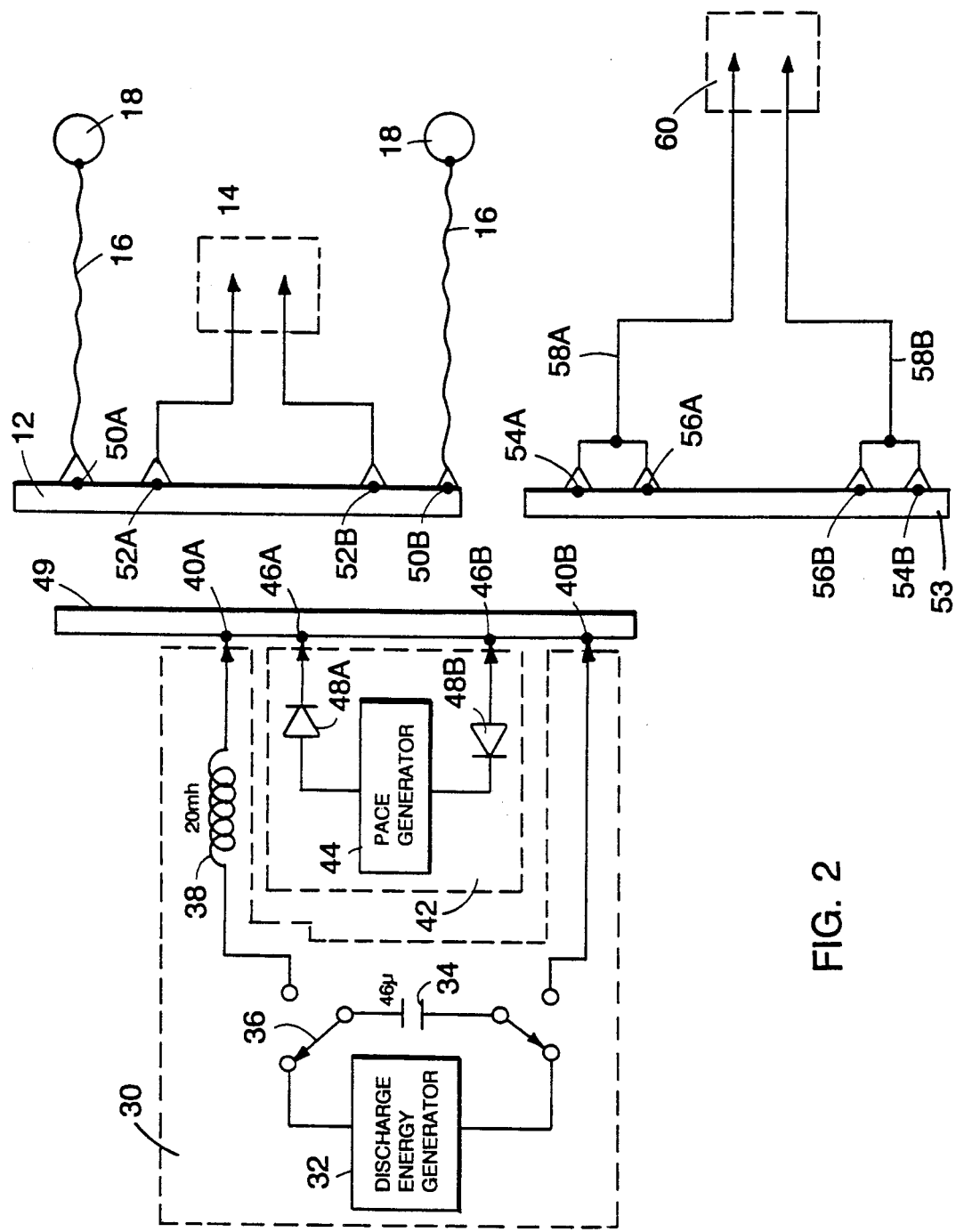
FIG. 2 is a schematic of the pacing circuitry and defibrillation circuitry in the unit of FIG. 1 and illustrates the circuitry interconnection of the invention.

The portable unit 10 includes a cable connector 12 for connecting a pacing electrode cable 14 and defibrillation electrode cables 16 to pacing circuitry and defibrillation circuitry, respectively (shown in FIGS. 2 and located within the unit. Hand held defibrillation electrode paddles 18, which mechanically support the defibrillation electrodes (shown in FIG. 8) are connected to the opposite end of the defibrillation electrode cables.

A screen 20 is provided on the portable unit for displaying operational modes and test results, which are programmed by various operator-controlled switches and knobs 22. Finally, the portable unit includes a power supply compartment 24 for holding a portable battery or other power source.

Referring to FIG. 2, the defibrillation circuitry 30 included in the portable unit comprises a discharge energy generator 32 for charging a discharge capacitor 34 to a defibrillation discharge energy specified by the operator. A switch 36 connects the capacitor to the discharge energy generator, and when the switch is activated by control circuitry (not shown) discharges the capacitor across the positive and negative defibrillation outputs 40A and 40B, respectively. The capacitor is preferably of 46 microfarads and can withstand 5000 volts across its terminals. An inductor 38 is in series with the capacitor for shaping the defibrillation pulse as the capacitor is discharged. The inductor is preferably of 20 millihenries and has an associated winding resistance of about 13 Ω.

The pacing circuitry 42 included in the portable unit comprises an electronic pace generator 44 for generating pacing stimuli and timing the delivery of the stimuli at the pacing circuitry positive and negative pacing outputs 46A and 46B, respectively. In series with the positive output 46A is a positive blocking diode 48A connected so that it is forward biased by the positive sense of the pace stimuli. Similarly, in series with the negative output 46B is a negative blocking diode 48B connected so that it is forward biased by the negative sense of the pace stimuli. The blocking diodes act to isolate the pace generator 44 from the typically high energy defibrillation discharge pulses, as discussed below. Preferably, both of the blocking diodes can withstand a reverse voltage of at least 5000 V and a forward current surge of at least 25A; such a surge could occur if the defibrillation circuit is unintentionally reverse connected to the pacing circuit.

Both the positive and negative defibrillation circuitry outputs 40A and 40B and the positive and negative pacing circuitry outputs 46A and 46B are tapped into an instrument connector 49 in the portable unit housing for connection with either a conventional mating connector 12, shown in FIG. 1, or a multifunction mating connector 53, described below. In the conventional mating connector 12 two pins 50A and 50B correspond to the positive and negative defibrillation circuitry outputs 40A and 40B, respectively, while two pins 52A and 52B correspond to the positive and negative pacing circuitry outputs 46A and 46B, respectively. The defibrillation pins 50A and 50B are connected to defibrillation cables 16 and corresponding electrode paddles 18, as shown in FIG. 1, for application of defibrillation discharge pulses to a patient. Likewise, the pacing pins 52A and 52B are connected to a pacing cable 14 for connection to pacing electrodes positioned on a patient.

In the multifunction mating connector 53, two pins 54A and 54B correspond to the positive and negative defibrillation circuitry outputs 40A and 40B, respectively, while two pins 56A and 56B correspond to the positive and negative pacing circuitry outputs 46A and 46B, respectively, just as in the conventional mating connector. However, in the multifunction connector the positive defibrillation output pin 54A and the positive pacing output pin 56A are connected together; similarly, the negative defibrillation output pin 54B and negative pacing output pin 56B are connected together.

The positive pin connection 54A to 56A and the negative pin connection 54B to 56B each are connected to a single positive cable line 58A and a single negative cable line 58B, respectively; the single pair of cable lines carry either defibrillation discharge pulses or pacing stimuli to a pair of multifunction electrodes (not shown) via a multi use connector 60. This multifunction electrode scheme provides an advantage over the conventional connector and electrode scheme by requiring only one pair of electrodes to be positioned on a patient, rather than both a defibrillation pair and a pacing pair. However, by connecting the positive circuitry pins together in the multifunction connector 53 itself, rather than in the instrument connector 49, the circuitry connector 49 is compatible with both the conventional and the multifunction electrode schemes and the operator may choose one as appropriate.

When in the multifunction connector and electrode configuration, output signals of the defibrillation circuitry are coupled to the pacing circuitry, and output signals of the pacing circuitry are coupled to the defibrillation circuitry. Thus the connector and circuit wiring must be able to carry the 25 A potentially developed in the discharge circuitry. Furthermore, the positive and negative connection pins in the connectors must meet high voltage and current specifications, as discussed below.

High energy discharge pulses generated by the discharge circuitry would damage the pace generator 44 of the pace circuitry if it were not isolated by the blocking diodes 48A and 48B. While the diodes are positioned to be forward biased by the pace generator pacing stimuli, the diodes are reversed biased with respect to the defibrillation circuit discharge pulses, and so block these pulses from the pace generator. Conversely, pacing stimuli generated by the pacing circuit are not blocked from coupling to the discharge circuit because the discharge circuit comprises only one passive component, an inductor, when the pacing circuit is operating. Because the inductor is designed to withstand the high energy defibrillation pulses, it easily withstands the much lower energy pacing stimuli. Thus, without the use of mechanical isolators such as relays, the blocking diodes isolate the pacing circuitry from the high energy defibrillation circuitry, while eliminating the typical space requirements and cost of mechanical isolators.

Figure 3A:
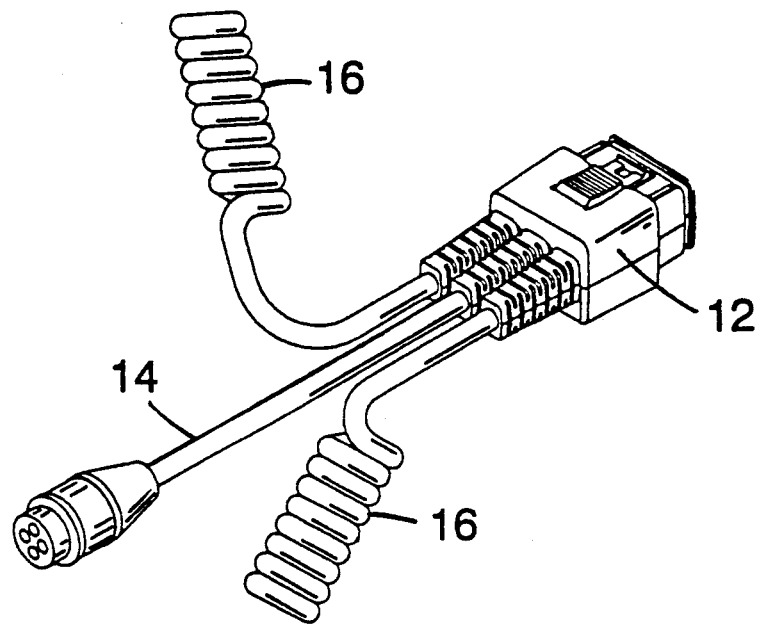
FIG. 3A is a perspective view of a conventional cable connector for use with the unit of FIG. 1.

Referring now to FIG. 3A, the conventional mating connector 12, also shown in FIG. 1, is connected to a pacing cable 14 which delivers the pacing circuitry outputs 46A and 46B (FIG. 2) to pacing electrodes placed on a patient. Separate defibrillation cables 16 deliver the defibrillation circuitry outputs 40A and 40B to defibrillation electrode paddles for placement on the patient. The two sets of cables and the disconnected output pins in the connector isolate the pacing and defibrillation circuitry from each other.

Figure 3B:
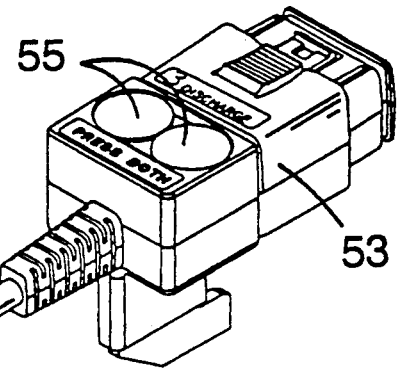
FIG. 3B is a perspective view of a multifunction cable connector for use with the unit of FIG. 1.
Figure 3B:
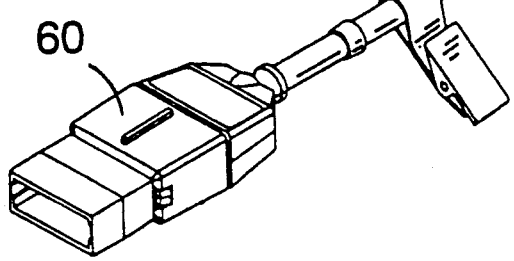

As shown in FIG. 3B, the multifunction mating connector 53 is connected to a single cable 58 for delivering both defibrillation pulses and pacing stimuli on a single positive cable line 58A and a negative cable line 58B (FIG. 2) The cable 58 leads to a multifunction electrode connector 60 which attaches to a single pair of patient electrodes for both transcutaneous pacing and defibrillation. The blocking diodes in the pacing circuit are the only means used for isolating the discharge pulses from the pacing circuitry in this multifunction scheme.

Figure 4A:
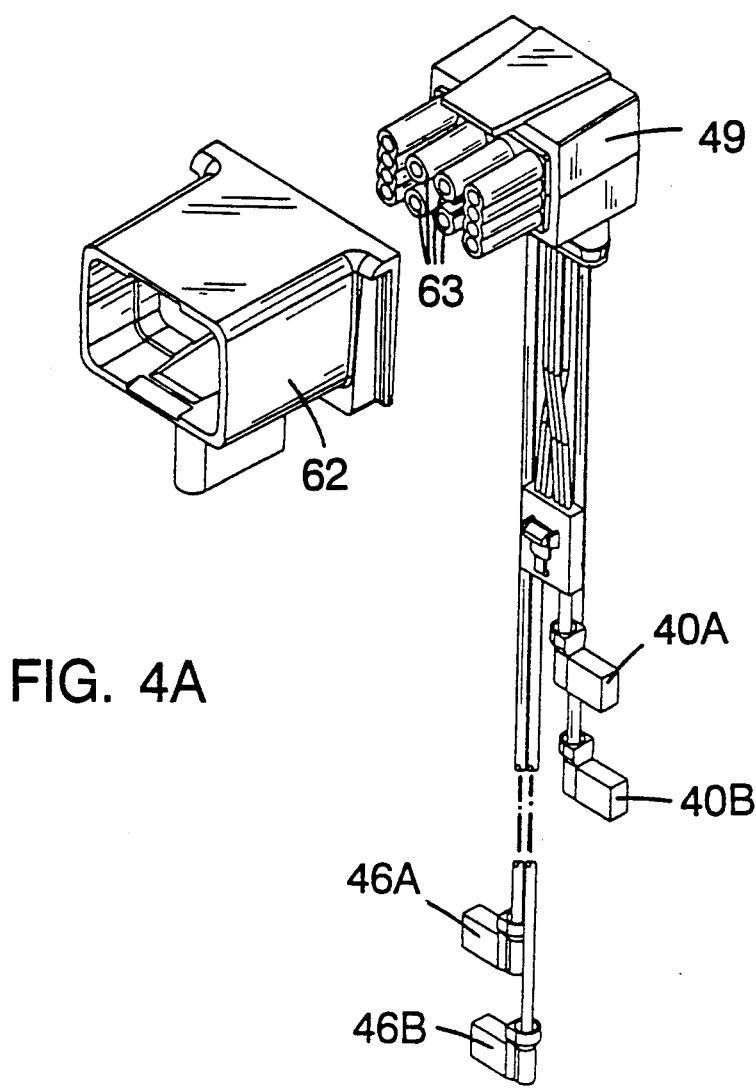
FIG. 4A is a perspective view of an instrument connector for use with the connectors of FIG. 3.
Figure 4B:
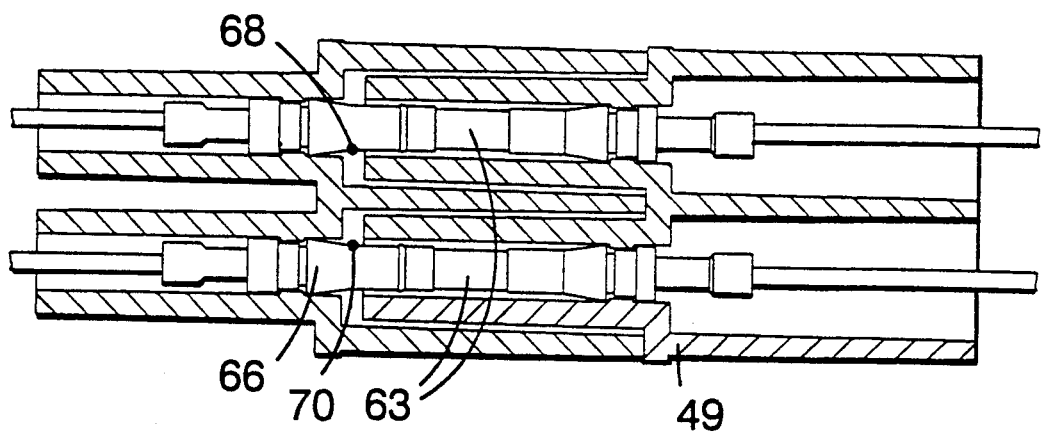
FIG. 4B is a cross sectional view taken at 4B—4B in FIG. 4A of two high voltage connection pins used in the cable connector of FIG. 4A.

The instrument connector 49, shown in FIG. 4A with its cover 62 pulled back, includes a number of pin connections, four of which are high voltage pins 63 positioned in high voltage labyrinth barrels. Each of the four barrels corresponds to one of the four outputs from the pacing and defibrillation circuitry, the positive and negative discharge outputs 40A and 40B and the positive and negative pacing outputs 46A and 46B. The other pins correspond to low voltage control leads and other wiring necessary for the circuitry.

When mated with either the conventional connector or the multifunction connector, the instrument connector high voltage barrel pins 63 mate with corresponding mating pins 66. The pin connections meet the IEC 601 Part 2 safety specification for defibrillation equipment; two adjacent pin connections can withstand the application of 7500 V between them, and the shortest electrical path 68-70 between two adjacent pin connections, called the creepage distance, is not less than 15 millimeters.

Figure 5:
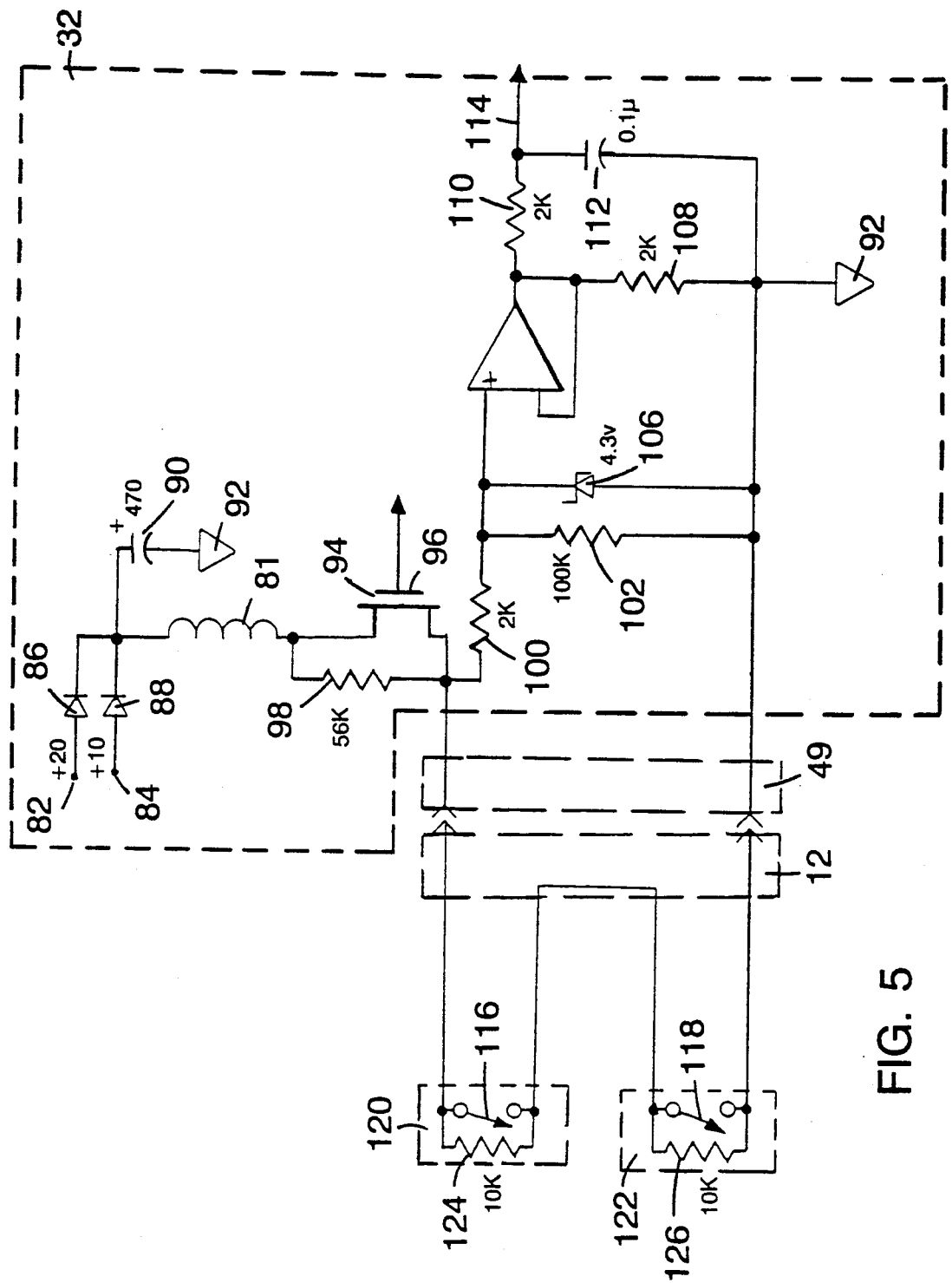
FIG. 5 is a schematic of the defibrillator electrode switches of the invention.

Referring now to FIG. 5, a relay coil or solenoid 81 actuates the medical grade relay switch 36 (FIG. 2). The relay coil is connected at one of its terminals to a dual 10 V and 20 V power supply 82, 84, and a 470 microfarad capacitor 90 connected to ground 92 for increasing the speed of the relay switch activation. The relay coil is actuated when its other terminal is connected to ground by the simultaneous closure of three switches. One of these switches is a MOS transistor switch 94 whose gate 96 is connected to a control circuit such as a microprocessor. A 56 K$\Omega$ shunt resistor 98 is connected across the MOS transistor for sensing the on or off state of the transistor, as discussed below. The MOS transistor is biased by a 2 K$\Omega$ resistor 100 and a 100 K$\Omega$ resistor 102.

The positive input of an operational amplifier 104 is connected to the MOS transistor sense network 100, 102 and a zener diode 106 having a 4.3 V avalanche voltage. The negative input and the output of the operational amplifier 104 are both connected to a network of two 2 K$\Omega$ resistors 108, 110 and a 0.1 microfarad capacitor 112 which together act as a voltage filter. In this configuration, the operational amplifier acts as a voltage follower for sensing the voltage level of the junction 97 of the MOS transistor and the defibrillation paddle switches, as described below. The voltage sense line 114 is connected to the same microprocessor that is connected to the gate of the MOS transistor, for control of the transistor, as described below. The microprocessor digitizes the analog sense voltage and activates the transistor accordingly.

The MOS transistor 94 and its shunt resistor 98 are connected to a pin in the instrument connector 49 (FIG. 2). When this connector is mated with either the conventional mating connector 12 (as shown) or the multifunction connector, the MOS transistor and its shunt resistor are connected in series with two mechanical switches 116, 118. The switches are rated to withstand the 1 A required by the discharge relay coil. Using the conventional connector 12, the first switch 116 is located in one electrode paddle 120 while the second switch 118 is located in the other electrode paddle 122. Conversely, if the multifunction connector is used as shown in FIG. 3B, both switches 116, 118 are connected to buttons 55 located on the multifunction connector housing 53. In either case, the switches are pressure activated by pressing a depressible push button. The switches are electrically connected in series via a jumper wire located in the connector; both the conventional and multifunction connectors provide this jumper wire. One of the other switch terminals is connected to ground via another pin in the connector and the corresponding pin in the instrument connector.

Each of the two switches 116, 118 has a 10 KΩ shunt resistor 124, 126, respectively, connected across the switch. Accordingly, when the switches are open, the discharge energy generation circuit is completed by the two shunt resistors and when the switches are closed the circuit is completed by two direct connections.

Both of the two mechanical switches and the MOS transistor switch can assume two impedance states: a high impedance state when open (or off), and a low impedance state when closed (or on). Being all connected in series, these three switches provide a scheme for sensing the appropriate time to activate the defibrillation discharge circuit and a scheme for verifying the integrity of the switches.

Both the mechanical switches and the MOS switch are normally open; the small current flowing in the shunt resistors 98, 124, 126 in this condition is low enough that the discharge relay coil 98 is not activated. In this condition, the voltage produced at the MOS-paddle switch junction 97 is determined by the bias resistors 98, 100, 102, 124, 126 and the supply voltage 82; this is about 2.6 volts for the resistor values shown in FIG. 5. Closure of either paddle switch 116, or 118 will remove one of the corresponding resistors 124, or 126 from the bias network by short it out. The resulting sense voltage 114 will therefor change to about 1.9 volts and be sensed by the microprocessor. The sensing of this condition triggers the microprocessor to indicate that the switches should be tested for failure.

When an operator presses both paddle switches, the MOS transistor is connected to ground, and the sense voltage decreases to a low value, at or near ground. Upon detection of this low voltage, the microprocessor triggers the gate 96 of the MOSFET, thereby turning the transistor on. Then with all three of the switches closed, the discharge relay activates.

When both switches are open, the MOS transistor may be tested in two ways. First, if it has failed in an "on" condition it will short out its shunt resistor 98, thereby increasing the sense voltage to a high level, between 4.0 and 4.5 volts, which is set by the zener diode 106 and the protection resistor 102. Second, if the transistor is in the "off" state, it may by turned "on" for a short time, say 2 msec, by the microprocessor, and the resultant voltage change monitored to check its integrity—if functioning the sense voltage would increase. Similarly, if the relay coil is broken, or its connector has a faulty contact, the loss of the bias voltage 82 will change the sense voltage 114 to indicate such a fault.

Table 1 below tabulates the six possible different voltage values at the sense line based on the six possible states of the three switches when the electrode resistors have the same shunt resistor values, as in FIG. 5.

TABLE 1

| Mech. Switch States: | Transistor/Relay States: | | |
|---|---|---|---|
| | Trans. Off | Trans. Shorted | Coil Open |
| Both Open | 2.57 V | 4.31 V | 0.72 V |
| Both Closed | 0.18 V | 0.55 V | 0.18 V |
| One Open | 2.04 V | 4.30 V | 0.58 V |

Based on the voltage values of Table 1 and a possible power supply range of 8 V–12 V, Table 2 below gives ranges for the sense voltage which indicate each of the various switch states, as well as electrode and transistor conditions.

TABLE 2

| Switch States: | Voltage Range |
|---|---|
| Trans. off, mech. switches open | 2.3 V–2.9 V |
| Trans. off, one mech. switch open | 1.7 V–2.3 V |
| Trans. off, mech. switches closed | 0.1 V–0.3 V |
| Relay coil unplugged | 1.0 V–1.4 V |
| Transistor shorted | >4.0 V |

Ideally, for a given power supply voltage, the three shunt resistors are chosen such that the voltage range for each of the possible switch conditions is distinct and the various ranges do not overlap. For example, the condition of both mechanical switches closed and the transistor turned off corresponds to a voltage range of 0.1 V–0.3 V, from Table 2, while the condition of one mechanical switch stuck closed and the transistor turned off corresponds to a voltage range of 1.7 V–2.3 V. The large differential between these two ranges ensures that the microprocessor does not misinterpret the switch conditions.

Further differentiation between each possible switch state could be accomplished using a different valued shunt resistor for each of the three resistors. Then eight different switch combinations may be detected. More generally, any circuit element having a characteristic impedance or voltage differential may be used in place of the shunt resistors. For example, a zener diode with a characteristic voltage drop may be shunted across the switches. In addition, circuit elements may be only temporarily connected in the circuit across the switches while the functionality of the switches is tested, rather than permanently installed in the circuit. In either case, the shunt resistance scheme allows for both precise triggering of the defibrillation discharge circuit and testing of the circuit's functionality.

Figure 6:
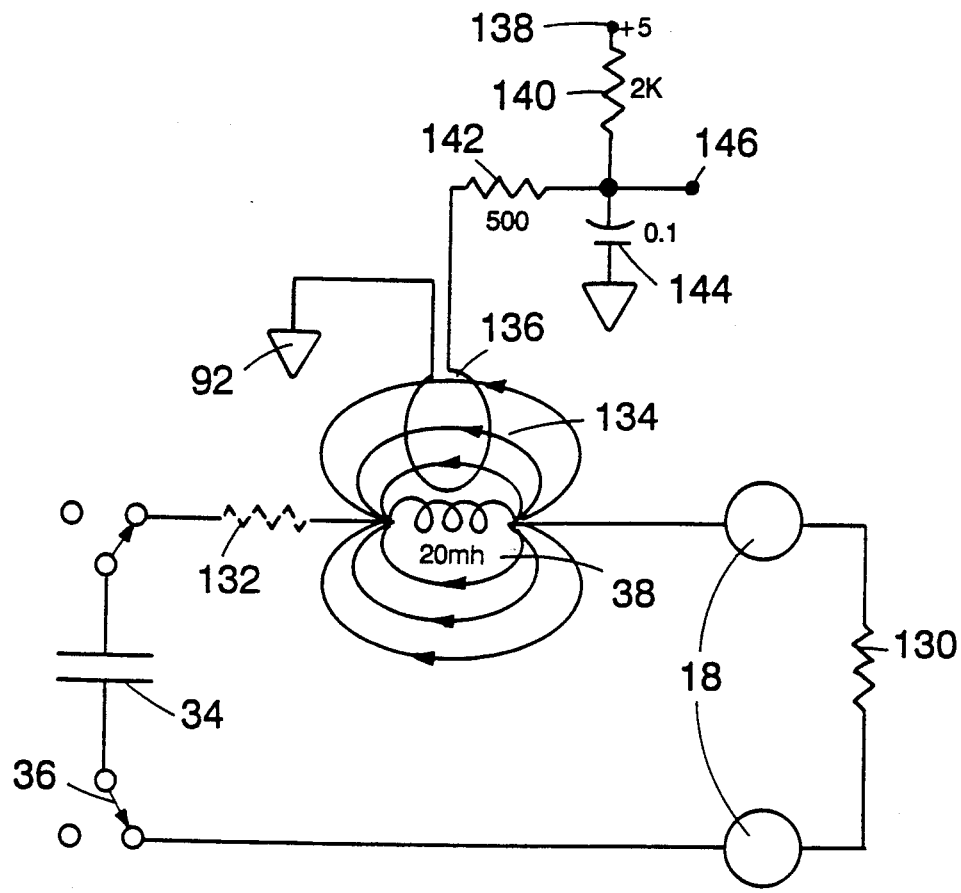
FIG. 6 is a schematic of the defibrillation discharge circuit and sensing circuit of the invention.

Referring now to FIG. 6, the defibrillation discharge circuit 30 is shown in detail. When the discharge energy switch 36 is closed across the circuit, the discharge energy capacitor 34 is discharged to the defibrillation electrode paddles 18, shown schematically. The capacitor forms an RLC circuit with the pulse shaping inductor 38, the thoracic resistance 130 of the patient to which the paddles 18 are connected, and a parasitic winding resistance 132 corresponding to the inductor winding. The characteristic values of each of the capacitive, resistive, and inductive components in the circuit determine the energy and shape of the defibrillation output pulses.

As the capacitor 34 is discharged, current flowing through the inductor winding generates lines of magnetic flux 134 around the winding turns and through the winding core. Taking advantage of this, a flux sense coil 136 is positioned with respect to the inductor such that the current in the inductor, and thus the current in the discharge circuit, can be monitored without direct connection to the circuit. The flux sense coil 136 comprises a conductor which encircles the inductor-produced lines of magnetic flux 134 at least once; electrical voltage is thereby developed in the sense coil in correspondence to the level of magnetic flux change, and thus, the level of current change in the inductor.

This flux coupling between the inductor and the sense winding is detected by circuitry comprising a bias voltage supply 138, set at 5 volts, two bias resistors 140, 142, set at 2 KΩ and 500 KΩ, respectively, and a smoothing capacitor 144, set at 0.1 microfarads. A voltage sense line 146 senses the voltage of the circuitry, which depends on the level of flux coupling in the sense coil and the design of the coil; the greater the number of sense coil turns, the higher the corresponding current and voltage. The voltage sense line is connected to a monitoring circuit, here a microprocessor, for determination of the discharge circuit current level, and hence the discharge pulse current waveform.

The microprocessor determines the pulse current waveform by sampling the voltage sense line 146 over the duration of the capacitor discharge to produce digitized voltage values. Then the voltage values are numerically integrated over the duration of the discharge and scaled by the inverse of the inductor value to determine corresponding current level values. These current values, which represent the pulse waveform current, are stored for further processing, such as peak current detection, discharge circuit load resistance determination, or pulse energy determination.

In place of a digital processor such as the microprocessor, hardware circuitry may process the sense coil signals to determine the discharge circuit's current waveform. Voltage values of the sense voltage line 146 are here digitized by a hardware analog-to-digital convertor and then integrated and scaled by an operational amplifier configured as an integrator. Peak current detection, load resistance determination, and energy determination processing may then be accomplished using further hardware circuit schemes.

Figure 7A:
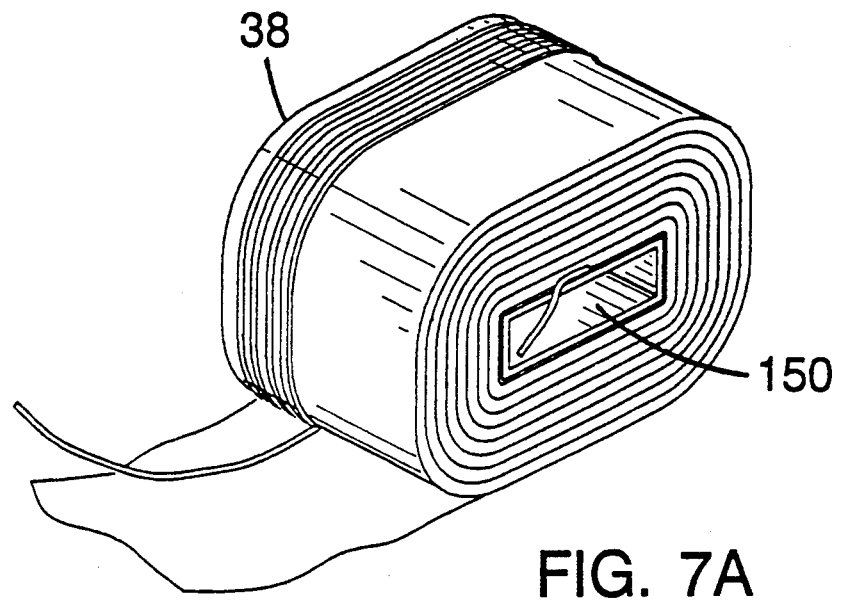
FIG. 7A is a perspective view of the inductor in the circuit of FIG. 6.
Figure 7B:
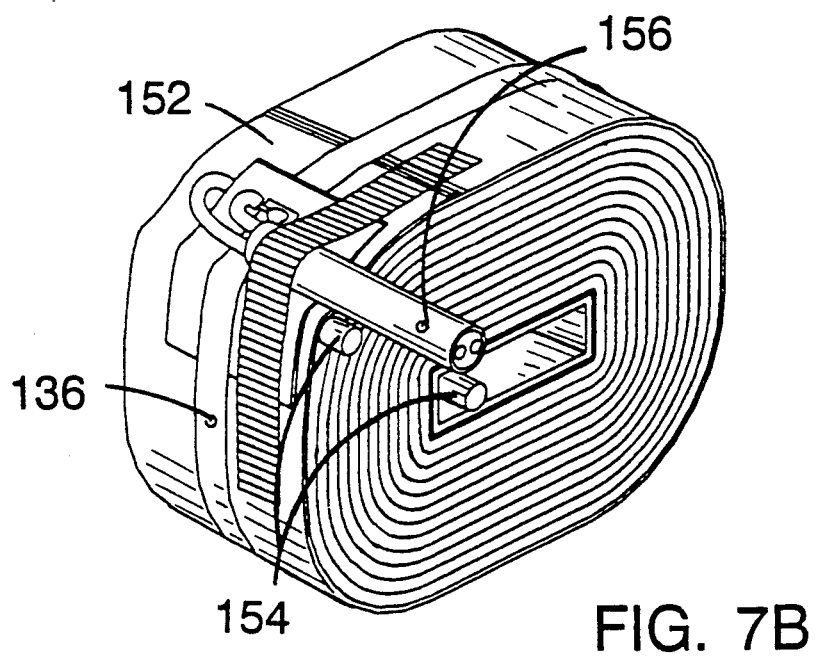
FIG. 7B is a perspective view of the inductor of FIG. 7A and the sense winding in the circuit of FIG. 6.

As shown in FIGS. 7A and 7B, the pulse shaping inductor 38 is constructed of conductive windings wound around an air core 150. Each winding layer is isolated by an insulating layer 152 of epoxy impregnated paper. Exit leads 154 for series connection in the discharge circuit are located at each end of the winding, which completes 1000 turns around the air core.

The sense coil 136 is wrapped around the outer winding of the inductor, and is electrically isolated from the inductor by several layers of epoxy impregnated paper. Other isolation schemes may be used, but must withstand the 7500 V which can develop between the coil and winding before breaking down. Sensing exit leads 156 are connected at each end of the coil for connection to the sense circuitry.

Additionally, the sense coil should occupy minimum space to keep the unit small and light. To effectively meet all of the above requirements, the sense coil is formed of a ⅛ inch-wide copper band comprising a 0.005 inch-thick copper layer and a 0.0015 inch-thick adhesive layer. This coil configuration is advantageously flat and easily positioned on the inductor winding. However, any effective conductor which can meet the discharge circuit's electrical requirements may be used as the coil, in any desired number of turns which generates a desired level of sense current and voltage.

Figure 8:
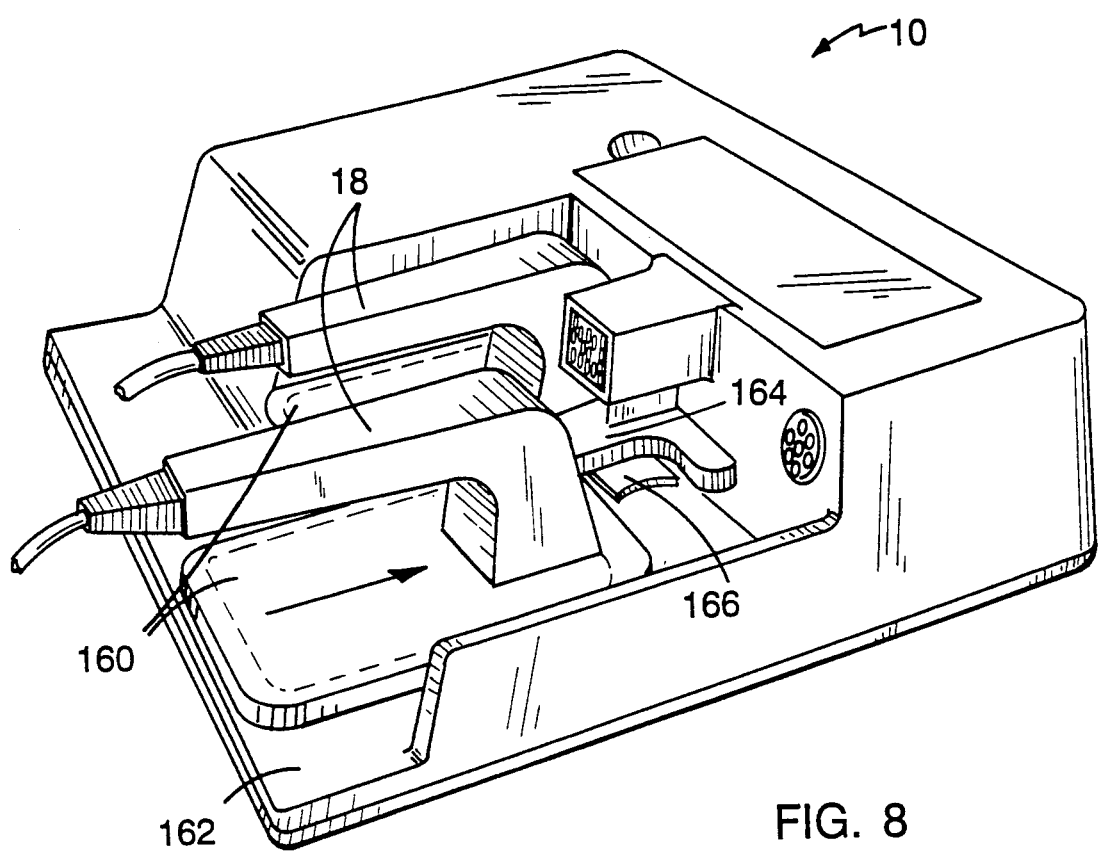
FIG. 8 is another perspective view of the pace maker and defibrillator unit of FIG. 1, taken from another angle and showing, with portions partially broken away, a short circuit bar for use with the defibrillator paddles.

Referring now to FIG. 8, the portable unit 10 includes design features for conveniently discharging the defibrillation discharge circuit to test the defibrillation discharge circuit's functionality. As shown in FIG. 2, the discharge circuit is connected via either a conventional mating connector or a multifunction connector to a pair of defibrillation electrodes. If the conventional scheme is used, the discharge circuit connects to a pair of hand held defibrillation paddles 18, shown in FIG. 8. Each paddle supports a defibrillation electrode 160 on its underside for application to the chest of a patient.

When not in use, the defibrillation paddles 18 are stored in a well 162 on the portable unit 10. The top side of the paddles are slid under a ledge 164 for securing the paddles in place on the unit housing with the electrodes 160 facing the housing. At the back of the well 162 is a conducting shorting bar 166 which lies on the well bottom and extends laterally under the ledge 164 to lie under the electrodes 160 when the paddles are pushed completely into the well. The lateral edges of the shorting bar 166 are flared upward to exert a positive contacting force on the electrodes when they are in place over the bar.

When the defibrillation discharge circuit is discharged and the electrode paddles 18 are in place in the well such that the electrodes 160 contact the shorting bar 166, a defibrillation pulse is discharged across a short circuit, rather than the thoracic resistance of a patient. As explained below, this discharge pulse is monitored to analyze its characteristics for verifying the acceptability of the pulse. The location of the shorting bar in the paddle well 162 is particularly advantageous because it prevents contact to the bar by an operator during a test discharge. As discussed above, the defibrillation circuit signals may reach quite high levels of voltage and energy, and thus operator coupling to the circuit must be prevented. In its position in the paddle well, the shorting bar is covered by the paddles and inaccessible to operator contact. However, the shorting bar may be located at any convenient position on the portable unit, or even detached from the unit.

Referring again to FIG. 6, during a discharge circuit test into the shorting bar, the thoracic load resistance 130 is replaced by a short circuit. As the defibrillation pulse is discharged into the short circuit, the flux sense coil 136 is coupled to the discharge inductor 38 to produce a sense voltage, and the sense voltage line 146 is monitored by a microprocessor to analyze the discharging pulse. Alternatively, a current transformer, or some other sensing component connected in the circuit could monitor the current.

Figure 9A:
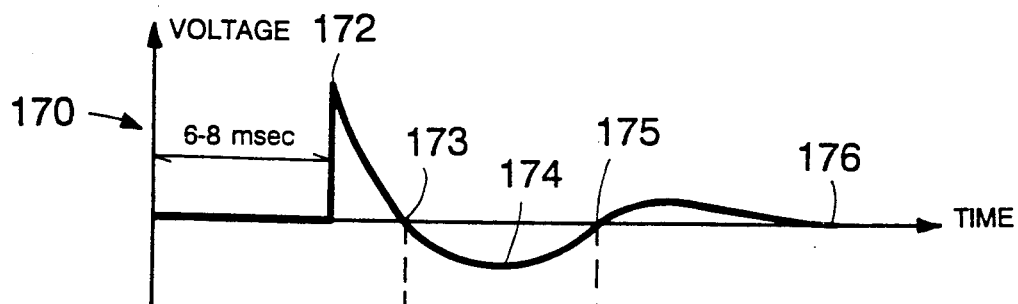
FIG. 9A is a plot of the voltage waveform developed by the sense winding of FIG. 7 in response to the current in the inductor of FIG. 7.

In the sense coil scheme described above, once the defibrillation discharge is initiated, the microprocessor (connected to the sense voltage line) digitally samples the sense voltage line at 60 microsecond intervals and stores the sampled values. The discharge is ended after 25 milliseconds when the discharge capacitor switch is disconnected from the inductor discharge circuit. A plot 170 of the stored voltage samples, as shown in FIG. 9A, illustrates that the voltage initially rises to some peak voltage 172, after which it falls to a valley voltage 174, and then levels off at a final voltage 176. The peak voltage 172 is typically reached about 6 milliseconds to 8 milliseconds after the discharge has been initiated, and the final voltage 176 is typically reached about 20 milliseconds later.

The microprocessor post-processes the stored voltage data to reconstruct the voltage waveform and convert it to a corresponding current waveform. First each voltage sample is measured to locate the first samples having a voltage value that is at least about 25% greater than the previous values. This indicates the start of the voltage waveform. Then a number of the previous values, say 6, are remeasured and averaged to determine the baseline, or quiescent, value of the waveform. This baseline is defined to be zero volts.

Having determined the waveform baseline, each sample value starting with the first sample above baseline is numerically integrated and scaled to produce current values corresponding to the voltage values. As part of the integration computation, the baseline value is subtracted from each integrated value so that only the waveform value is added in the integration. At the end of the integration interval, the last current value should be zero. If it is not zero, the last current magnitude is measured and proportionately subtracted from all the previous current values to set the baseline value at zero.

Figure 9B:
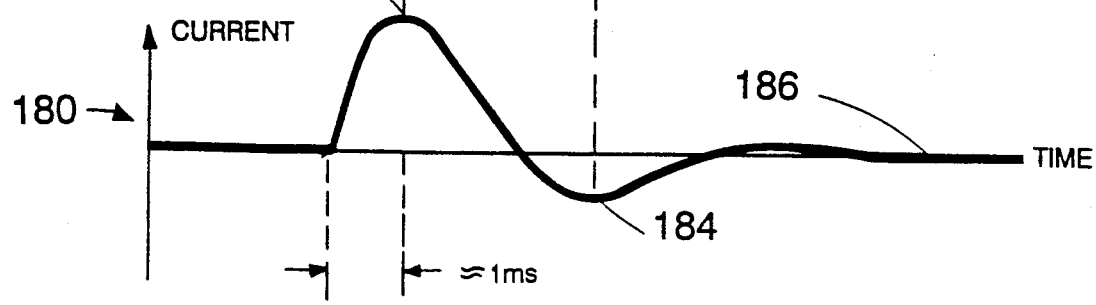
FIG. 9B is a plot of the current waveform corresponding to the voltage waveform of FIG. 9A when that waveform is integrated.

A plot of the corresponding current waveform as shown in FIG. 9B illustrates that the current rises to a peak current value 182 and then falls off to a valley current value 184, after which it settles to a final current value 186, which is adjusted to be zero. The current peak 182 corresponds to the first zero crossing 173 of the voltage waveform and the current valley 184 corresponds to the second zero crossing 175 of the voltage waveform. The magnitude of the current peak and valley is determined by the value of the discharge inductor's parasitic resistance (132 in FIG. 6), and thus any changes in the resistance are reflected in the sampled values. As discussed below, the waveform values are adjusted accordingly to compensate for any resistance changes.

The current peak value 182 is detected by measuring the current value samples located between 0.5 milliseconds and 2.5 milliseconds. Once a peak value is located, it is added to the three current samples preceding it and the three current samples following it to produce a 7 sample peak sum. Similarly, the current valley value 184 is detected by measuring the current value samples located between 3.0 milliseconds and 6.0 milliseconds. Once a valley value is located, it is added to the three current samples preceding it and the three current samples following it to produce a 7 sample valley sum. The peak and valley sums are then stored for later computations.

A ratio of the peak current sum to the valley current sum is then computed. This ratio is used to determine any necessary adjustments in the peak current to compensate for changes in the discharge inductor's parasitic resistance. As mentioned above, this resistance may vary; it is particularly dependent on temperature. At 25° C., the resistance of the 1000 turn winding is about 13Ω, but the resistance changes by −0.4% for each °C. drop. Thus, for the range of expected operating temperatures, the parasitic resistance ranges from 10 Ω–14 Ω.

As the parasitic resistance varies, the peak current varies accordingly, because the resistance is part of the RLC circuit which generated the pulse current. The valley current also varies according to the parasitic resistance, and is more strongly effected by resistance changes than is the peak current. With a high load resistance, such as the typical 50 Ω thoracic patient resistance, the current waveform would exhibit no valley current. At a load resistance of about 25 Ω, the circuit would be critically damped, and exhibit a slight current valley. With a short circuit load, as in the discharge test described above, the magnitude of the valley reaches about 30-35% of the peak current magnitude. If the parasitic resistance decreases due to a temperature decrease, the valley current will increase more than the peak current will increase and will thereby produce a smaller peak to valley current ratio than at a higher temperature. In the limiting case, if the resistance of the RLC circuit dropped to zero, the current peak and valley would be equal and the waveform would never dampen out.

The current peak is adjusted based on a comparison of the computed peak to valley current ratio and a range of prespecified peak to valley current ratios. At 25° C. and a discharge energy of 100 joules, the ratio is expected to be 3.1. If the temperature is below 25° C. that ratio will be lower than 3.1, while the ratio will be higher than 3.1 if the temperature is above 25° C.; the change in the parasitic resistance described above effects this ratio change.

If the computed ratio is less than 3.1, then the adjusted peak current sum $I_{peak}'$ is computed based on the measured peak current $I_{Peak}$ as follows:

$$I_{peak}' = I_{peak} + 7 * [13 * |k| - 40];$$

if the computed ratio is more than 3.1, an adjusted peak current sum $I_{peak}'$ is computed based on the measured peak $$I_{peak}' = I_{peak} + 7 * [10 * |R| - 31],$$

where R is the peak to valley current ratio.

The peak current sum is not adjusted if the computed ratio is more than 4.0. This ratio value indicates that a defibrillation discharge to a resistive load (such as a patient), and not a test discharge to the shorting bar, occurred. As explained above, the load resistance of the discharge circuit determines the peak and valley pulse currents, and thus the peak to valley current ratio. When a defibrillation pulse is discharged to a patient, there is little or no current valley, and the ratio is above 4.0. Thus no special test indicator must be operator-activated when a test is to be performed; the microprocessor automatically detects this via the peak to valley current ratio. All that is required is for the energy of the test to be set at 100 joules—the current waveform computations are based on this energy value. If the ratio is above 4.0, no test results are displayed to the operator.

For test discharges, the adjusted peak current value is compared to a preset range of current values to determine if the defibrillation pulse is acceptable. If the peak current falls between 65 A and 78 A, the microprocessor displays a "Test OK" message on the portable unit's screen. Conversely, if the peak current does not fall within the range, a "Test Failed" message is displayed for the operator.

Further waveform analysis may be completed. For example, the total energy of the pulse may be computed by numerically integrating the pulse current value, squared, multiplied by the inductor parasitic resistance over the duration of the pulse. Thus, the total energy of the pulse, $E_{total}$, may be expressed as:

$$E_{total} = \int (i^2 R)\, dt$$

where R is the inductor parasitic resistance, i is the pulse current value, and the integral is taken over the duration of the pulse. Based on this energy value, and the initial capacitor voltage sample value, the capacitor value may be verified.

Other waveform analysis includes determining the pulse width by detecting the zero crossings of the current waveform. Additionally, the rise and fall times of the waveform may be computed based on the voltage sample values and their corresponding sample times.

As an alternative to the microprocessor, analog and digital hardware may be implemented to perform the various waveform computations. For example, as described above, an operational amplifier configured as an integrator may be used to complete the various integration calculations. Other hardware circuitry corresponding to the sampling, scaling, and comparing functions of the microprocessor may similarly be implemented.

Other embodiments are within the following claims. For example, certain of the features relating to the defibrillator could be incorporated in a unit not having pacemaking capability.

What is claimed is:

1. A method for discharging a defibrillation energy pulse discharge circuit to analyze defibrillation pulses generated by the discharge circuit to test that the pulses are acceptable, the discharge circuit comprising an electrical capacitor for storing defibrillation pulse energy before the pulse is discharged and an electrical inductor in series with the capacitor and having a characteristic inductance for shaping the discharge pulses and a characteristic resistance, the method comprising the following steps, each performed by electronic circuitry:

discharging a defibrillation pulse generated by the discharge circuit into a short circuit, detecting one or more parameters representative of the shape of the defibrillation pulse as the pulse is discharged, comparing the detected parameters to predetermined values characteristic of the shape of an acceptable pulse, and based on the comparing step, providing an output indicative of whether the pulse is acceptable.

2. The method of claim 1 wherein discharging a defibrillation pulse comprises charging the capacitor to a prespecified energy and then discharging the capacitor into the short circuit.

3. The method of claim 1 further comprising the step of determining if the defibrillation pulse is a test pulse or a pulse delivered to a patient, and based on the determination, providing said output only if the pulse is a test pulse.

4. The method of claim i wherein the discharge circuit output is electrically connected to each electrode of a pair of electrodes for delivering defibrillation pulses to a patient, and wherein the discharge circuit is enclosed in a housing on which is externally positioned a conductive shorting bar, and wherein discharging a defibrillation pulse comprises touching the pair of electrodes to the shorting bar.

5. The method of claim 4 wherein each electrode is located on one face of a corresponding hand held paddle and the housing comprises holding means for securely storing each of the paddles on the housing with the paddle faces on which the electrodes are located facing toward the housing, the holding means positioned over the shorting bar, wherein discharging the defibrillation pulse further comprises securing the paddles under the holding means such that the electrodes contact the shorting bar.

6. The method of claim 1 wherein said one or more parameters representative of the shape of the defibrillation pulse comprise a parameter representative of a defibrillation pulse current and said detecting step comprises measuring said parameter representative of the defibrillation pulse current.

7. The method of claim 6 wherein the detecting step further comprises measuring a sense voltage developed between ends of a sense winding wound around, the inductor with at least one turn between the ends for developing a sense voltage between the ends in response to the defibrillation pulse current in the inductor.

8. The method of claim 7 further comprising numerically integrating the sensed voltage to determine corresponding defibrillation pulse current values.

9. The method of claim 8 further comprising the step of determining a peak defibrillation pulse current value and a valley defibrillation pulse current value.

10. The method of claim 9 further comprising the steps of determining a ratio of the peak defibrillation pulse current to the valley defibrillation pulse current, determining if the defibrillation pulse is a test pulse or a pulse delivered to a patient by comparing the ratio to a prespecified ratio, and based on the comparison, providing said output only if the pulse is a test pulse.

11. The method of claim 9 further comprising determining a ratio of the peak defibrillation pulse current value to the valley defibrillation pulse current value and based on the ratio, adjusting the peak defibrillation pulse current value to produce an adjusted peak pulse current value to account for any temperature-induced changes in the characteristic resistance of the inductor, and wherein said comparing step further comprises comparing the adjusted peak pulse current value with a prespecified peak pulse current to determine whether the defibrillation pulse is acceptable.

12. The method of claim 11 wherein adjusting the peak defibrillation pulse current value comprises increasing the peak defibrillation pulse current value if the characteristic resistance has increased and decreasing the peak defibrillation pulse current value if the characteristic resistance has decreased.

13. The method of claim 11 wherein the prespecified peak pulse current used in said comparing step comprises a range of peak pulse currents, and wherein said comparing step determines that said defibrillation pulse is acceptable if the adjusted peak pulse current falls within said range of peak pulse currents.

14. The method of claim 6 wherein the detecting step further comprises sampling the detected parameter at each of a plurality of spaced time intervals during discharge of the defibrillation pulse to produce sample values.

15. Apparatus for discharging a discharge circuit to analyze defibrillation pulses generated at an output of the discharge circuit to test that the pulses are acceptable, the apparatus comprising:

a discharge circuit having an output and comprising an electrical capacitor for storing defibrillation pulse energy before the pulse is discharged and an electrical inductor in series with the capacitor and having a characteristic inductance for shaping the discharge pulses and a characteristic resistance, a conductive short circuit bar for connection across the output of the discharge circuit to discharge a defibrillation pulse into the short circuit bar, means for detecting one or more parameters representative of the shape of the defibrillation pulse as it is discharged, means for comparing the detected parameters to predetermined values characteristic of the shape of an acceptable defibrillation pulse, and means for providing an output signal, based on the comparison, indicative of whether the defibrillation pulse is acceptable.

16. The apparatus of claim 15 wherein said one or more parameters representative of the shape of the defibrillation pulse comprise a parameter representative of a defibrillation pulse current and said means for detecting one or more parameters representative of the shape of the defibrillation pulse comprises means for measuring said parameter representative of the defibrillation pulse current.

17. The apparatus of claim 16 wherein the parameter detecting means comprises a sense winding wound around the inductor with at least one turn between ends of the winding for developing a sense voltage between the ends in response to the current in the inductor.

18. The apparatus of claim 17 further comprising sampling means for sampling the detected parameter at each of a plurality of spaced time intervals during discharge of the defibrillation pulse to produce sample values.

19. The apparatus of claim 18 further comprising means for integrating the sensed voltage to determine corresponding defibrillation current values.

20. The apparatus of claim 19 further comprising peak detector means for determining a peak defibrillation pulse current and a valley defibrillation pulse current.

21. The apparatus of claim 20 wherein the comparing means comprises means for producing a representation of the peak defibrillation pulse current, and means for computing a ratio of the peak defibrillation pulse current to the valley defibrillation pulse current and, based on the ratio, for adjusting the representation of the peak defibrillation pulse current to account for any temperature-induced changes in the characteristic resistance of the inductor, and for comparing the adjusted representation of the peak defibrillation pulse current with a prespecified peak pulse current to determine whether the defibrillation pulse is acceptable.

22. The apparatus of claim 15 wherein said one or more parameters representative of the shape of the defibrillation pulse comprise a defibrillation pulse current and said means for detecting one or more parameters representative of the shape of the defibrillation pulse comprises means for measuring the defibrillation pulse current.

23. A discharge pulse delivery apparatus for delivering defibrillation pulses to a patient and for discharging a discharge circuit to analyze defibrillation pulses generated at an output of the discharge circuit to test that the pulses are acceptable, the apparatus comprising:

a discharge circuit having an output and comprising an electrical capacitor for storing defibrillation pulse energy before the pulse is discharged and an electrical inductor in series with the capacitor and having a characteristic inductance for shaping the discharge pulses and a characteristic resistance, a conductive short circuit bar for connection across the output of the discharge circuit to discharge a defibrillation pulse into the short circuit bar, means for detecting one or more parameters representative of the shape of the defibrillation pulse as it is discharged, means for comparing the detected parameters to predetermined values characteristic of the shape of an acceptable defibrillation pulse, means for providing an output signal, based on the comparison, indicative of whether the defibrillation pulse is acceptable, and a pair of electrodes, wherein the output of the discharge circuit is electrically connected to each electrode of the pair of electrodes for delivering defibrillation pulses to a patient, and wherein the discharge circuit is enclosed in a housing on which is externally positioned the conductive short circuit bar such that the circuit is discharged into the short circuit bar by touching the pair of electrodes to the bar.

24. The apparatus of claim 23 wherein each electrode is located on one face of a corresponding hand held paddle and the housing comprises holding means for securely storing each of the paddles on the housing with the paddle faces on which the electrodes are located facing toward the housing, the holding means positioned directly over the short circuit bar, wherein the discharge circuit is discharged into the short circuit bar when the paddles are secured under the holding means such that the electrodes contact the bar.

* * * * *

UNITED STATES PATENT AND TRADEMARK OFFICE
CERTIFICATE OF CORRECTION

PATENT NO. : 5,249,573

DATED : October 5, 1993

INVENTOR(S) : Randall W. Fincke and Michael L. Lopin

It is certified that error appears in the above-identified patent and that said Letters Patent is hereby corrected as shown below:

Column 2, line 40, after "be", delete the ",".

Column 4, line 8, after "and", insert "6".

Column 13, line 54, "claim i" should be --claim 1--.

Column 14, line 13, after "around", delete the ",".

Signed and Sealed this

Twenty-sixth Day of July, 1994

Attest:

BRUCE LEHMAN

*Attesting Officer*    *Commissioner of Patents and Trademarks*